United States Patent
Ahotupa et al.

(12)

(10) Patent No.: US 6,204,295 B1
(45) Date of Patent: *Mar. 20, 2001

(54) ANTIOXIDANT COMPOUNDS

(75) Inventors: Markku Ahotupa, Turku; Lauri Kangas, Raisio, both of (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/309,285

(22) Filed: May 11, 1999

Related U.S. Application Data

(62) Division of application No. 09/180,088, filed as application No. PCT/FI97/00266 on May 2, 1997, now Pat. No. 5,929,123.

(30) Foreign Application Priority Data

May 2, 1996 (GB) .................................. 9609171

(51) Int. Cl.⁷ ................................. A61K 31/135
(52) U.S. Cl. ............................................. 514/651
(58) Field of Search ............................... 514/651

(56) References Cited

U.S. PATENT DOCUMENTS 5,491,173  2/1996  Toivola et al.
5,929,123  * 7/1999  Ahotupa et al. ..................... 514/651

FOREIGN PATENT DOCUMENTS

| 4320896A1 | 1/1995 | (DE) . |
| WO93/11757 | 6/1993 | (WO) . |
| WO93/19746 | 10/1993 | (WO) . |
| WO96/07402 | 3/1996 | (WO) . |

OTHER PUBLICATIONS

"Droloxifene (3-hydroxytamoxifen) has membrane antioxidant ability: potential relevance to its mechanism of therapeutic action in breast cancer", H. Wiseman et al., *Cancer Letters*, vol. 66 (1992) pp. 61–68.

"The antioxidant action of tamoxifen and its metabolites: Inhibition of lipid peroxidation", H. Wiseman et al. *FEBS Letters*, vol. 263, No. 2 (Apr. 1990), pp. 192–194.

* cited by examiner

*Primary Examiner*—Raymond Henley, III
(74) *Attorney, Agent, or Firm*—Burns, Doane, Swecker & Mathis LLP

(57) ABSTRACT

A new use of halogenated triphenylethylene derivatives for lowering levels of serum lipid peroxides and for the prevention or treatment of oxidative tissue damage induced by lipid peroxidation is disclosed. The new use includes the prevention or treatment of artherosclerosis, ischemic injury, psoriasis, inflammatory diseases, such as inflammatory bowel disease, or cardiovascular disorders, such as coronary heart disease, cardiac ischemic injury and post-ischemic cardiac arrhythmias, or the treatment of AIDS.

6 Claims, 2 Drawing Sheets

ANTIOXIDANT COMPOUNDS

This application is a divisional of application Ser. No. 09/180,088, filed Nov. 2, 1998, now U.S. Pat. No. 5,929,123; which in turn is a 371 of Application No. PCT/FI97/00266, filed May 2, 1997.

TECHNICAL FIELD OF THE INVENTION

The present invention relates to a new medical use of, and method of treatment using, halogenated triphenylethylene derivatives of formula (I), for lowering levels of serum lipid peroxides, and for the prevention or treatment of oxidative tissue damage induced by lipid peroxidation. In particular, the present invention provides a new use of compounds of formula (I) for the prevention or treatment of atherosclerosis, ischemic injury, psoriasis, inflammatory diseases such as inflammatory bowel disease, or cardiovascular disorders such as coronary heart disease, cardiac ischemic injury and post-ischemic cardiac arrhythmias, or for the treatment of AIDS.

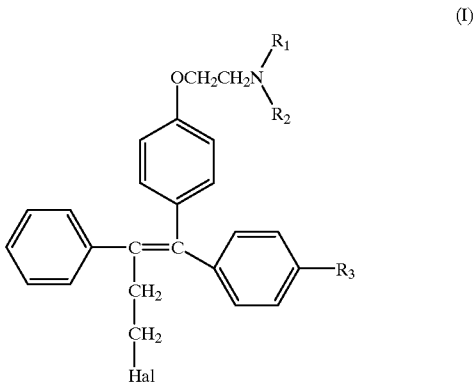

wherein Hal is halogen, $R_1$ and $R_2$ are independently hydrogen or $C_1$–$C_4$ alkyl, and $R_3$ is hydrogen or hydroxy, or pharmaceutically acceptable salts thereof.

BACKGROUND OF THE INVENTION

Medicinal antioxidants are compounds that may be used for the prevention of tissue damage induced by lipid peroxidation (Halliwell, B., FASEB J. 1:358–364, 1987). During lipid peroxidation free radicals interact with polyunsaturated fatty acids to form lipid peroxyl radicals, which produce lipid hydroperoxides and further lipid peroxyl radicals. This peroxidative cascade may eventually consume an essential part of the membrane lipid, which may lead to changes in membrane permeability and ultimately in cell death. The peroxidative degradation of lipids also leads to the formation of potentially toxic products such as malondialdehyde.

Numerous recent studies indicate that peroxidation of low density lipoproteins contribute to the formation and progression of atherosclerosis. Various antioxidants have been shown to decrease arterial lesions in animal models of atherosclerosis. So it is believed that the reduction of the atherogenic risk is associated with the reduction of atherogenic lipid peroxides which are essentially transported in the LDL fraction in the serum.

There is evidence that free radical induced lipid peroxidation occurs in ischemic injury, e.g. in cardiac ischemic injury following coronary thrombosis or in reperfusion ischemic injury during surgery. The importance of lipid peroxidation in tissue damage associated with ischemia is supported by the protective effect of natural and synthetic antioxidants or antioxidant enzymes in diverse ischemic models. It is believed that reduction of the lipid peroxidation associated with ischemia protects the vital organs, such as the cardiovascular system and cerebral tissue, from oxidative damage, e.g. in patients recovering from myocardial infarction or during surgery.

NADPH oxidase of polymorphonuclear leucocytes (neutrophils) is the source of superoxide radical anion and other reactive oxygen species which are important in the defence against pathogens. Tissue damage due to the uncontrolled production of reactive oxygen species by activated neutrophils is known to occur in connection with diseases like psoriasis or acute or chronic inflammatory diseases, e.g. inflammatory bowel disease. It is believed that compounds which inhibit the oxidative burst of the activated neutrophils can be of therapeutic interest in the prevention and treatment of these diseases. Furthermore, recent studies indicate that increased oxygen radical production by neutrophils (oxidative stress) is present in HIV-infected patients and that the oxygen radical overproduction can increase the expression and replication of HIV-1 (Jarstrand, C. et al., Chemico-Biological Interactions 91, 141–146, 1994; Schreck, R. et al., The EMBO Journal, 10, 8, 2247–2258, 1991; Favier, A. et al., Chemico-Biological Interactions 91, 165–180, 1994 and Fuchs, J. et al., Medical Hypotheses, 36, 60–64, 1991). Therefore it is believed that compounds which inhibit the oxidative burst of the activated neutrophils can be of therapeutic interest also in the treatment of AIDS.

SUMMARY OF THE INVENTION

In a first aspect the present invention provides a new medical use of compounds of formula (I) in the manufacture of medicaments for use in lowering levels of serum lipid peroxides.

In another aspect the present invention provides a new medical use of compounds of formula (I) in the manufacture of medicaments for use in the prevention or treatment of oxidative tissue damage induced by lipid peroxidation. In particular, the present invention provides a new use of compounds of formula (I) in the manufacture of medicaments for use in the prevention or treatment of atherosclerosis, ischemic injury, psoriasis, inflammatory diseases, such as inflammatory bowel disease, or cardiovascular disorders, such as coronary heart disease, cardiac ischemic injury and post-ischemic cardiac arrhythmias, and in the treatment of AIDS.

In another aspect, the present invention provides a new medical use of compounds of formula (I) in the manufacture of medicaments for use in protection of organs, particularly the cardiovascular system and cerebral tissue, from oxidative damage induced by lipid peroxidation associated with ischemia, particularly in patients recovering from myocardial infarction or during surgery.

In another aspect, the present invention provides a method for lowering levels of serum lipid peroxides in patients comprising administering to a patient in need thereof a serum lipid peroxides lowering amount of a compound of formula (I) or a pharmaceutically acceptable salt thereof.

In another aspect, the present invention provides a method for the prevention or treatment of oxidative tissue damage induced by lipid peroxidation in patients comprising administering to a patient in need thereof an effective amount of a compound of formula (I) or a pharmaceutically acceptable salt thereof. In particular, the present invention provides a method for the prevention or treatment of atherosclerosis, ischemic injury, psoriasis, inflammatory diseases, such as inflammatory bowel disease, or cardiovascular disorders, such as coronary heart disease, cardiac ischemic injury and post-ischemic cardiac arrhythmias, or for the treatment of AIDS in patients comprising administering to a patient in need thereof an effective amount of a compound of formula (I) or a pharmaceutically acceptable salt thereof.

In another aspect, the present invention provides a method for protection of organs, particularly the cardiovascular system and cerebral tissue, from oxidative damage induced by lipid peroxidation associated with ischemia, particularly in patients recovering from myocardial infarction or during surgery, comprising administering to a patient in need thereof an effective amount of a compound of formula (I) or a pharmaceutically acceptable salt thereof.

In yet another aspect, the present invention provides a method for inhibiting the production of reactive oxygen species by activated neutrophils comprising administering to a patient in need thereof a reactive oxygen species production inhibiting amount of a compound of formula (I) or a pharmaceutically acceptable salt thereof.

DETAILED DESCRIPTION OF THE INVENTION

Figure 1:
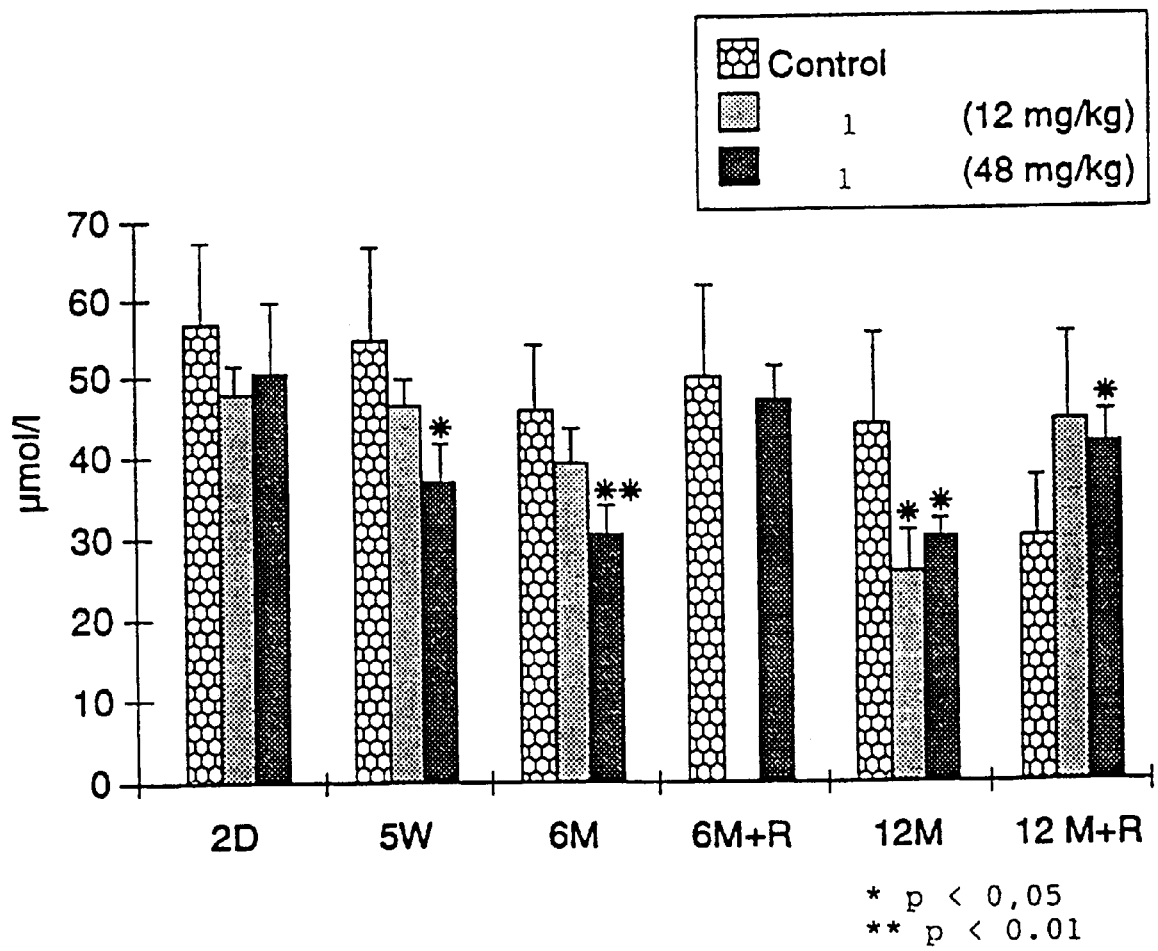
FIG. 1 shows serum diene conjugation in rats treated with different doses of a compound of the invention.

It has now been found that triphenylethylene derivatives of formula (I)

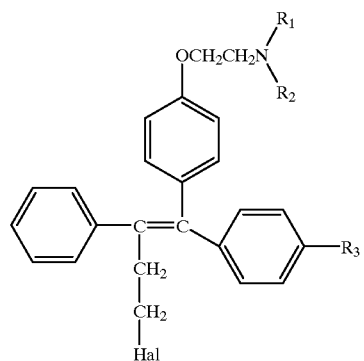

(I)

wherein Hal is halogen, $R_1$ and $R_2$ are independently hydrogen or $C_1$–$C_4$ alkyl, and $R_3$ is hydrogen or hydroxy, or pharmaceutically acceptable salts thereof, inhibit microsomal lipid peroxidation, decrease serum levels of lipid peroxides in vivo and inhibit the production of reactive oxygen species by activated neutrophils. Therefore the compounds of formula (I) are useful as medicinal antioxidants in the treatment or prevention of diseases is which oxidative processes play a role.

The invention encompasses pure (Z) and (E) isomers of the compounds of formula (I) as well as mixtures thereof. The preferred compounds of formula (I) are those in which halogen is chlorine, bromine or iodine. The particularly preferred compounds of formula (I) are those in which halogen is chlorine, bromine or iodine, $R_1$ and $R_2$ are independently hydrogen or methyl, and $R_3$ is hydroxy.

The following compounds of formula (I) are examples of the preferred compounds:
4-chloro-1,2-diphenyl-1-[4-[2-(N,N-dimethylamino)ethoxy]phenyl]-1-butene,
4-iodo-1,2-diphenyl-1-[4-[2-(N,N-dimethylamino)ethoxy]phenyl]-1-butene,
4-chloro-1,2-diphenyl-1-[4-[2-(N-methylamino)ethoxy]phenyl]-1-butene,
4-chloro-1-(4-hydroxyphenyl)-1-[4-[2-(N,N-dimethylamino)ethoxy]-phenyl]-2-phenyl-1-butene,
4-chloro-1-(4-hydroxyphenyl)-1-[4-[2-(N-methylamino)ethoxy]phenyl]-2-phenyl-1-butene, and
4-chloro-1,2-diphenyl-1-[(4-aminoethoxy)phenyl]-1-butene.

Examples of the particularly preferred compounds are:
4-chloro-1-(4-hydroxyphenyl)-1-[4-[2-(N,N-dimethylamino)ethoxy]-phenyl]-2-phenyl-1-butene, and
4-chloro-1-(4-hydroxyphenyl)-1-[4-[2-(N-methylamino)ethoxy]phenyl]-2-phenyl-1-butene.

Compounds of formula (I) have been described earlier in e.g. EP 95875 and U.S. Pat. No. 5,491,173 as antiestrogenic compounds for use in the treatment of hormone dependent tumours. The compound of formula (I) wherein Hal is Cl, $R_1$ and $R_2$ are methyl, and $R_3$ is hydrogen, Z-isomer, named toremifene, is currently clinically used in the treatment of estrogen receptor positive breast cancer.

The compounds of formula (I) or pharmaceutically acceptable salts thereof can be prepared using methods described in EP 95875 and U.S. Pat. No. 5,491,173.

The compound of the invention may be administered in a variety of ways including orally, parenterally or transdermally using conventional forms of preparations, such as capsules, tablets, granules, powders, suppositories, injections, patches, suspensions and syrups. The term "effective amount" means an amount of compound of the invention which is capable of providing a medicinal antioxidant effect. The compound of the invention may be administered monthly, weekly or daily or several times a day depending upon the patient's needs. A typical daily oral dosage is within the range of from about 1 mg to about 500 mg, preferably from about 5 to about 100 mg, of the active compound. However, the dosage may be properly varied depending on the age, body weight and conditions of the patient as well as on the administration method. The compound of the invention may be administered alone or together with other active compounds.

The compositions according to the invention can be prepared by the methods commonly employed in the art. In addition to the active compound the compositions may contain pharmaceutically acceptable additives commonly used in the art, such as carriers, binders, excipients, lubricants, suspending agents and diluents. The amount of the active compound in the compositions of the invention is sufficient to produce the desired therapeutical effect, for example about 1 mg to 500 mg, more preferably from about 5 to about 100 mg, in unit dosage for both oral and parenteral administration.

EXPERIMENTS

The following compounds of the invention were tested in the experiments:
Compound 1=4-chloro-1,2-diphenyl-1-[4-[2-(N,N-dimethylamino)ethoxy]phenyl]-1-butene, Z-isomer (toremifene),
Compound 2=4-chloro-1-(4-hydroxyphenyl)-1-[4-[2-(N,N-dimethylamino)ethoxy]phenyl]-2-phenyl-1-butene, Z-isomer Compound 3=4-chloro-1-(4-hydroxyphenyl)-1-[4-[2-(N-methylamino)ethoxy]phenyl]-2-phenyl-1-butene, Z-isomer Compound 4=4-iodo-1,2-diphenyl-1-[4-[2-(N,N-dimethylamino)ethoxy]phenyl]-1-butene, Z-isomer Compound 5=4-chloro-1,2-diphenyl-1-[4-[2-(N,N-dimethylamino)ethoxy]phenyl]-1-butene, E-isomer.

METHODS

Preparation of Microsomes

Adult male Sprague-Dawley rats were decapitated, and the liver was excised and chilled in ice-cold 0.25 M sucrose solution. A 20% (w/v) liver homogenate was prepared in the sucrose solution (0° C.) with a homogenizer. Microsomes were prepared from the postmitochondrial (12000×g for 10 min at 4° C.) supernatant fluid by centrifugation (105000×g for 10 min at 4° C.).

Estimation of Antioxidant Potency

The antioxidant properties of the compounds were estimated by their potency to inhibit t-butylhydroperoxide (t-BuOOH) or ascorbate/ADP-$FeCl_3$-induced lipid peroxidation in rat liver microsomes in vitro. In the t-BuOOH assay the buffer (50 mM sodium carbonate, pH 10.2, with 0.1 mM EDTA) was pipetted in a volume of 0.8 ml in the luminometer cuvette. 20 µl of diluted rat liver microsomes (final concentration 1.5 µg protein/ml) was added, followed by 6 µl of luminol (0.5 mg/ml) and test compounds. The reaction was initiated by 0.05 ml of 0.9 mM t-BuOOH at 33° C. The chemiluminescence was measured for about 45 min and the area under the curve was calculated. In the ascorbate/ADP-$FeCl_3$ assay microsomes (final concentration 1.2 mg protein/ml) in 20 mM phosphate buffer, including 90 mM KCl, were incubated for 20 min at 37° C. in the presence of ascorbate (0.5 mM final concentration; pH of the buffer 6.0), ADP and $FeCl_3$ (final concentrations 0.85 and 0.05 mM, respectively) and test compounds. Total incubation volume was 0.5 ml. The incubation was stopped by addition of 0.5 ml of 30% trichloroacetic acid plus 0.05 ml 2% butylated hydroxytoluene in ethanol. The extent of lipid peroxidation was estimated by the amount of thiobarbituric acid (TBA) reactive material formed.

Isolation of Neutrophils

Neutrophils were isolated from 30 ml freshly drawn heparinized whole blood, after dextran sedimentation of erythrocytes for 30 min. The leucocyte rich plasma was layered over an equal volume of Percoll (Sigma) and centrifuged at 400 g for 15 min. Erythrocytes, contaminating the neuthrophil pellet, were destroyed by osmotic lysis with 0.87% $NH_4Cl$ (pH 7.0). Neutrophils were washed with PBS (pH 7.1) and centrifuged at 200 g for 10 min. Cells were resuspended in fresh HBS (containing 0.8 g NaCl, 0.4 g KCl, 0.06 g $Na_2HPO_4×2H_2O$, 0.06 g $KH_2PO_4$, 0.1 g $MgSO_4×7H_2O$ and 1 g glucose in 1000 ml of distilled water; pH adjusted to 7.4 by 7% $NaHCO_3$) and counted before use.

Measurement of Reactive Oxygen Production by Neutrophils

One ml of cell suspension (final cell count $10^6$ cells/ml) and the test compound was placed in cuvettes. Production of reactive oxygen by neutrophils ("oxidative burst") was stimulated by addition of phorbol-myristate-acetate (PMA; final concentration 2 µM). The luminol enhanced chemiluminescence was recorded.

In Vivo Studies

Test compound was given to six-week old female Sprague-Dawley rats daily by oral gavage at doses of 12 and 48 mg/kg for 12 months. The vehicle, carboxymethyl cellulose (0.5%), was given to control animals. Five rats per dose group were killed after 2 days, 5 weeks, 3, 6 and 12 months of dosing. Further groups were allowed to recover for 13 weeks without treatment after 6 and 12 months' dosing. The serum levels of lipid peroxides were measured by two different methods (diene conjugation and TBA-reactive material). For the measurement of diene conjugation, lipids extracted from serum samples (100 µl) by chloroform/methanol (2:1), dried under nitrogen and redissolved in cyclohexane, were analyzed spectrophotometrically (at 234 nm). For the analysis of TBA-reactive material serum samples (100 µl) were diluted in phosphate buffer and heated together with a TBA solution (375 mg/ml) in a boiling water bath for 15 min. The tubes were cooled, and the absorbances measured at 535 nm.

Results

The $IC_{50}$ values for the inhibition of microsomal lipid peroxidation by test compounds is shown in Table 1. $IC_{50}$ value means concentration of test compound that inhibits lipid peroxidation by 50%. For estimation of the $IC_{50}$ values, concentration ranges from 1 nM to 1 mM were used.

TABLE 1

$IC_{50}$ values (µM) for the inhibition of microsomal lipid peroxidation

| | Lipid peroxidation initiated by | |
|---|---|---|
| Compound | Ascorbate/ADP-$FeCl_3$ | t-Butylhydroperoxide |
| 1 | 18 | 450 |
| 2 | 8 | 0.18 |
| 3 | 31 | 27 |
| 4 | 3 | 0.38 |
| 5 | 36 | 410 |
| 17β-estradiol | 300 | 4.6 |
| diethylstilbestrol | 17 | 1.7 |
| α-tocopherol | 43 | 2.0 |
| butylated hydroxyanisole | 0.2 | 1.1 |

Table 1 shows that in the ascorbate/ADP-$FeCl_3$ test the antioxidant potency of the compounds of the invention were comparable to known antioxidant α-tocopherol. In the t-BuOOH test the antioxidant potency of the compounds 2 and 4 of the invention were even stronger than that of the known synthetic antioxidant butylated hydroxyanisole while the other compounds showed weaker effect.

The effect of the test compounds in inhibiting the production of reactive oxygen species by activated neutrophils is shown in Table 2.

TABLE 2

Inhibition of NADPH oxidase of the neutrophils.

| Compound | 1 mM | $IC_{50}$ (µM) |
|---|---|---|
| 1 | >99% | 2.17 |
| 2 | >99% | 2.12 |
| 4 | >99% | 2.32 |
| 17-β-estradiol | no effect | |
| diethylstilbestrol | >99% | 8 |
| Trolox (in $H_2O$) | no effect | |
| Trolox (in EtOH) | 59% | |

Table 2 shows that the compounds of the invention were more potent that the known antioxidant Trolox in inhibiting the production of reactive oxygen species by activated neutrophils.

Figure 2:
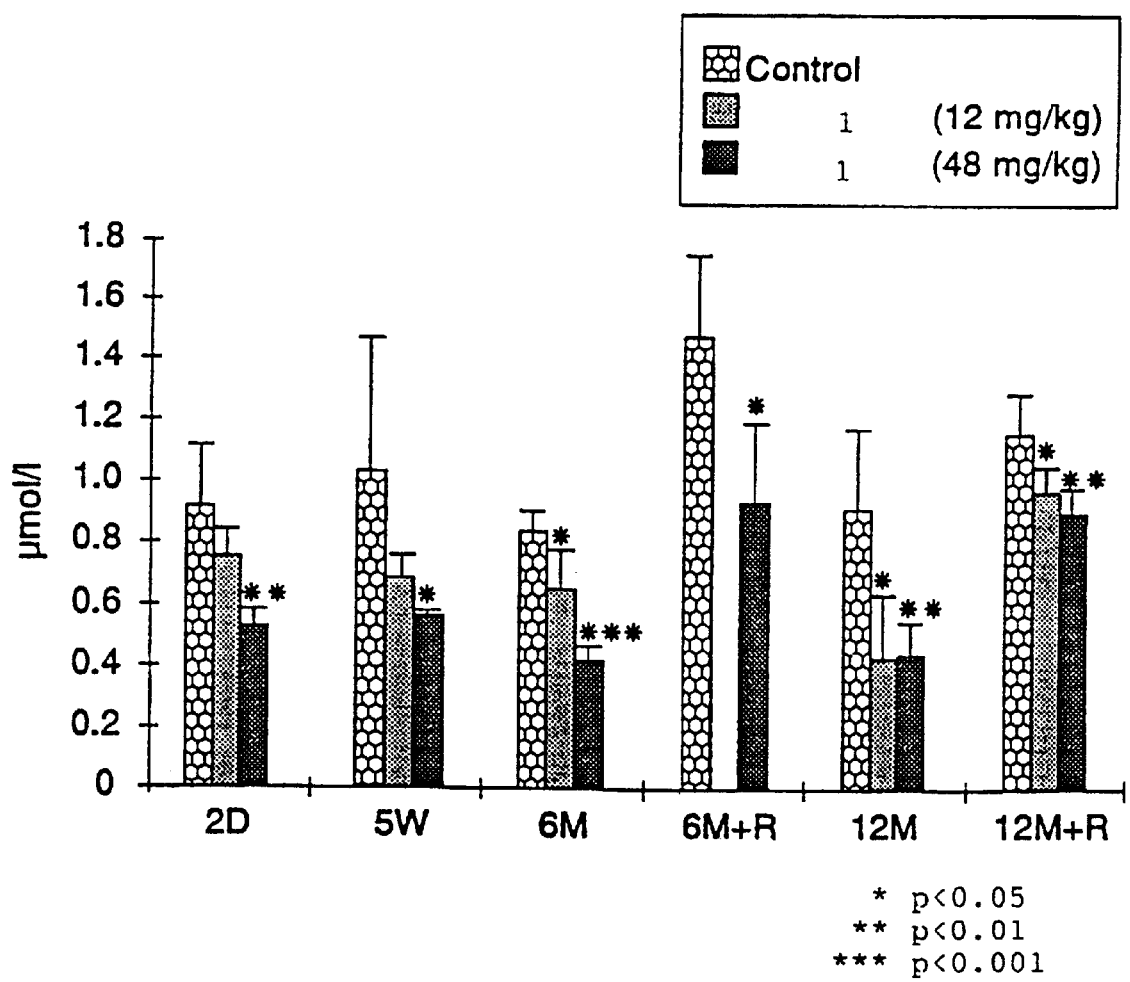
FIG. 2 shows serum TBA reactive material in rats treated with different doses of a compound of the invention.

The effect of compound 1 on the serum levels of lipid peroxides as measured by the two different methods (diene conjugation and TBA-reactive material) after 2 days (2 D), 5 weeks (5 W), 6 and 12 months (6 M and 12 M) treatment is shown in FIGS. 1 and 2, respectively. The groups which were allowed to recover for 13 weeks without treatment after 6 and 12 months dosing is shown as 6 M+R and 12 M+R. The results show that compound 1 was effective in decreasing both diene conjugation and TBA-reactive material in rats.

What is claimed is:

1. A method of therapy involving protection of organs from oxidative damage induced by lipid peroxidation comprising administering to a subject in need of such therapy an effective amount of a compound of formula (I)

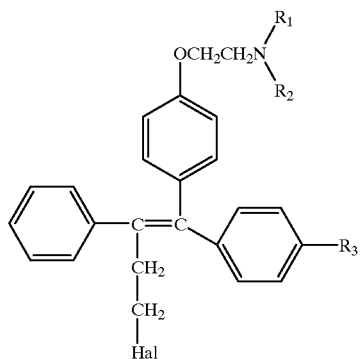

(I)

or a pharmaceutically acceptable salt thereof.

2. The method of claim 1, wherein the organ to be protected is the cardiovascular system or cerebral tissue.

3. The method of claim 2, wherein the subject to be treated is recovering from myocardial infarction.

4. The method of claim 1, which is effected during surgery.

5. A method of therapy for treating a condition involving inhibiting the production of reactive oxygen species by activated neutrophils comprising administering to a subject in need of such therapy an effective amount of a compound of formula (I)

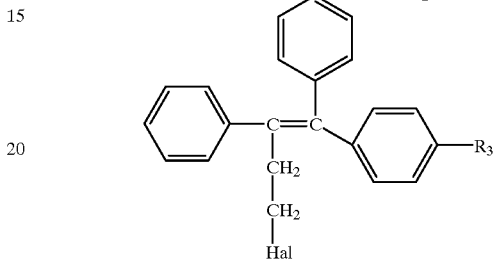

(I)

or a pharmaceutically acceptable salt thereof.

6. The method of claim 5, wherein the condition to be treated is selected from the group consisting of psoriasis, inflammatory diseases or disorders, and AIDS.

* * * * *